United States Patent
Kim et al.

(10) Patent No.: US 8,647,683 B2
(45) Date of Patent: Feb. 11, 2014

(54) **WHITENING COMPOSITION FOR EXTERNAL SKIN APPLICATION CONTAINING *OLDENLANDIA DIFFUSA* WILLD, *RHEUM UNDULATUM*, AND *BROUSSONETIA KAZINOKI* EXTRACT**

(75) Inventors: Eun Joo Kim, Suwon-si (KR); Ho Sik Rho, Yongin-si (KR); Su Jong Kim, Yongin-si (KR); Eun Jeong Moon, Seoul (KR); Ga Young Cho, Yongin-si (KR); Hye Yoon Park, Anyang-si (KR); Jung Chul Ha, Yongin-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 155 days.

(21) Appl. No.: 13/130,992

(22) PCT Filed: Nov. 23, 2009

(86) PCT No.: PCT/KR2009/006883
§ 371 (c)(1),
(2), (4) Date: Jul. 25, 2011

(87) PCT Pub. No.: WO2010/062087
PCT Pub. Date: Jun. 3, 2010

(65) Prior Publication Data
US 2011/0274635 A1    Nov. 10, 2011

(30) Foreign Application Priority Data

Nov. 25, 2008   (KR) .................. 10-2008-0117660

(51) Int. Cl.
| | |
|---|---|
| *A61K 36/00* | (2006.01) |
| *A61K 8/00* | (2006.01) |
| *A61K 8/18* | (2006.01) |
| *A61Q 5/08* | (2006.01) |
| *A61Q 19/02* | (2006.01) |

(52) U.S. Cl.
USPC .............................. 424/725; 424/62

(58) Field of Classification Search
None
See application file for complete search history.

(56) References Cited

FOREIGN PATENT DOCUMENTS

| CN | 1762324 A | 4/2006 |
|---|---|---|
| DE | 102006015574 A1 * | 10/2007 |
| DE | 102006015575 A1 * | 10/2007 |
| JP | 2005298505 A * | 10/2005 |
| JP | 2007106675 A * | 4/2007 |
| KR | 10-1993-0010548 B1 | 10/1993 |
| KR | 10-2006-0121496 A | 11/2006 |
| KR | 10-0702519 B1 | 3/2007 |

OTHER PUBLICATIONS

Jang et al. (1997) Cosmetics and Toiletries magazine vol. 112, 59-62.*
Hwang et al. (2007) J. Toxicology and Environmental Health, Part A, 70: 393-407.*
Xin, "Future whitening cosmetics natural ingredients—rhubarb", *Foreign medical the (TCM Volume)*, (1996).
Office Action from Chinese Application No. 200980142720.9 (mailed Oct. 17, 2012).
International Search Report (Form PCT/ISA/210) for corresponding International Application No. PCT/KR2009/006833.
Written Opinion (Form PCT/ISA/237) for corresponding International Application No. PCT/KR2009/006833.

* cited by examiner

*Primary Examiner* — Chris R Tate
*Assistant Examiner* — Russell Fiebig
(74) *Attorney, Agent, or Firm* — Merchant & Gould P.C.

(57) ABSTRACT

Disclosed is a whitening composition for external skin application. Containing one or more of *Oldenlandia diffusa* Willd extract, *Rheum undulatum* extract and *Broussonetia kazinoki* extract as an effective ingredient, the whitening composition for external skin application exhibits superior melanogenesis inhibition and skin whitening effect. Accordingly, it may be used in various skin whitening cosmetics.

4 Claims, No Drawings

WHITENING COMPOSITION FOR EXTERNAL SKIN APPLICATION CONTAINING *OLDENLANDIA DIFFUSA* WILLD, *RHEUM UNDULATUM*, AND *BROUSSONETIA KAZINOKI* EXTRACT

This application is a National Stage Application of PCT/KR2009/006883, filed 23 Nov. 2009, which claims benefit of Serial No. 10-2008-0117660, filed 25 Nov. 2008 in the Republic of Korea and which applications are incorporated herein by reference. To the extent appropriate, a claim of priority is made to each of the above disclosed applications.

TECHNICAL FIELD

This disclosure relates to a whitening composition for external skin application one or more of *Oldenlandia diffusa* Willd extract, *Rheum undulatum* extract and *Broussonetia kazinoki* extract as an effective ingredient.

BACKGROUND ART

Human skin color is determined by a lot of factors including activity of melanin-producing melanocytes, distribution of blood vessels, skin thickness, and presence of pigments such as carotenoids, bilirubin, etc. Above all, skin color is determined primarily by the black pigment melanin produced by melanocytes through the action of tyrosinase and other enzymes. The production of melanin is affected by genetic factors, physiological factors such as hormones and stress, and environmental factors such as UV. Existing in skin, melanin protects the skin from UV or the like. But, overly produced melanin is known to accelerate pigmentation and skin aging and to play an important role in skin cancer. In order to treat or ameliorate abnormal or excessive melanin pigmentation caused by exposure to UV or the like, ascorbic acid, kojic acid, arbutin, hydroquinone, glutathione, derivatives thereof or tyrosinase-inhibiting substances have been added to cosmetics or medicines. However, their use is restricted because of insufficient skin whitening effect, skin safety issue, stability when added to cosmetics, or the like.

DISCLOSURE

Technical Problem

The inventors have researched to solve the aforesaid problems. As a result, they have found that a composition containing one or more of *Oldenlandia diffusa* Willd extract, *Rheum undulatum* extract and *Broussonetia kazinoki* extract as an effective ingredient exhibits superior skin whitening effect with no harm to the skin.

Accordingly, this disclosure is directed to providing a whitening composition for external skin application having superior skin whitening effect with no skin trouble.

Technical Solution

There is provided a whitening composition for external skin application containing one or more of *Oldenlandia diffusa* Willd extract, *Rheum undulatum* extract and *Broussonetia kazinoki* extract as an effective ingredient.

A whitening composition for external skin application according to an embodiment may contain *Oldenlandia diffusa* Willd extract and *Rheum undulatum* extract as an effective ingredient. The *Oldenlandia diffusa* Willd extract and the *Rheum undulatum* extract may be contained at a weight ratio of 1-4:1-4.

A whitening composition for external skin application according to another embodiment may contain *Oldenlandia diffusa* Willd extract and *Broussonetia kazinoki* extract as an effective ingredient. The *Oldenlandia diffusa* Willd extract and the *Broussonetia kazinoki* extract may be contained at a weight ratio of 1-4:1-4.

A whitening composition for external skin application according to another embodiment may contain *Oldenlandia diffusa* Willd extract, *Rheum undulatum* extract and *Broussonetia kazinoki* extract as an effective ingredient. The *Oldenlandia diffusa* Willd extract, the *Rheum undulatum* extract and the *Broussonetia kazinoki* extract may be contained at a weight ratio of 1-4:1-4:1-4.

Advantageous Effects

A whitening composition for external skin application containing one or more of *Oldenlandia diffusa* Willd extract, *Rheum undulatum* extract and *Broussonetia kazinoki* extract as an effective ingredient provides 1.5 to 2 times superior melanogenesis inhibition and skin whitening effect, as compared to those containing *Oldenlandia diffusa* Willd, *Rheum undulatum* or *Broussonetia kazinoki* extract alone, and is safe to skin. Accordingly, it may be used in various skin whitening cosmetics.

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

This disclosure provides a whitening composition for external skin application comprising one or more of *Oldenlandia diffusa* Willd extract, *Rheum undulatum* and *Broussonetia kazinoki* extract as an effective ingredient.

*Oldenlandia diffusa* Willd is a medicinal herb that has been known and used widely not only in Oriental medicine but also in folk remedies. *Oldenlandia diffusa* Willd is a Rubiaceae family plant growing naturally in dense and shady forests of southern China, Southeast Asia and Korea's Jeju Island. In Chinese traditional medicine, it has been used to treat liver cancer, lung cancer and colon cancer, to alleviate fever, and to detoxicate. *Oldenlandia diffusa* Willd contains betulin, betulinic acid, ursolic acid, oleanolic acid, stigmasterol, β-sitosterol, β-glycyrrhetinic acid, ρ-coumaric acid, glucoside, hentriacontane, etc. and is known to have anticancer activity, anti-inflammatory effect and antiviral effect.

However, these traditionally known effects of *Oldenlandia diffusa* Willd are entirely different from the skin whitening effect.

For *Rheum undulatum*, root or stem of *Rheum undulatum* Linne is used. In addition, root or stem of *Rheum palmatum* Linne, *Rheum tanguticum* Maximowicz, *Rheum coreanum* Nakai, *Rheum palmarum* Linne var. *palmatum*), or interspecific hybrids thereof (Polygonaceae) may also be used. It contains emodin, chrysophanol, rhein, aloe-emodin, glucogallin, rhaponticin, etc. and is known to have pharmacological activities including antibacterial, antiviral, immune complex purifying and promoting, hepatic cell inhibition alleviating, rabbit serum cholesterol normalizing, diuretic, bacterial collagenase inhibiting, and angiotensin-converting enzyme inhibiting activities.

*Broussonetia kazinoki* (paper mulberry) includes *Broussonetia kazinoki* Sieb, *Broussonetia papyrifera* Vent, etc. *Broussonetia kazinoki* is a deciduous broad-leaved shrub distributed in most parts of Korea (mainly in the southern provinces), China, Taiwan, Japan, or the like. It grows at the sunny foot of the mountain, around the field, or the like. Its bast fiber has been used in the manufacture of paper. Also, it is known to have various medicinal effects, including tonifying, eye brightening, impotency treating, dropsy treating, energizing, diuretic, stroke ameliorating, blood purifying, and macular degeneration inhibiting effects.

In addition, *Broussonetia kazinoki* has tyrosinase activity inhibiting effect and provides good skin whitening effect through its antioxidative action. However, when used alone, it does not exhibit sufficient skin whitening effect because of instability and difficulty of formulation.

In an embodiment, a whitening composition for external skin application comprising *Oldenlandia diffusa* Willd extract and *Rheum undulatum* extract as an effective ingredient may comprise the *Oldenlandia diffusa* Willd extract and the *Rheum undulatum* extract at a weight ratio of 1-4:1-4. And, a whitening composition for external skin application comprising *Oldenlandia diffusa* Willd extract and *Broussonetia kazinoki* extract as an effective ingredient may comprise the *Oldenlandia diffusa* Willd extract and the *Broussonetia kazinoki* extract at a weight ratio of 1-4:1-4. Further, a whitening composition for external skin application comprising all of *Oldenlandia diffusa* Willd extract, *Rheum undulatum* extract and *Broussonetia kazinoki* extract as an effective ingredient may comprise the *Oldenlandia diffusa* Willd extract, the *Rheum undulatum* extract and the *Broussonetia kazinoki* extract at a weight ratio of 1-4:1-4:1-4.

If the weight ratio of the *Oldenlandia diffusa* Willd extract, the *Rheum undulatum* extract and the *Broussonetia kazinoki* extract is outside the aforesaid range, a superior skin whitening effect may not be attained.

The *Oldenlandia diffusa* Willd extract, the *Rheum undulatum* extract and the *Broussonetia kazinoki* extract included in the whitening composition for external skin application may be prepared by a known method.

The whitening composition for external skin application containing one or more of *Oldenlandia diffusa* Willd extract, *Rheum undulatum* extract and *Broussonetia kazinoki* extract as an effective ingredient provides superior melanogenesis inhibition and skin whitening effect, as compared to those containing *Oldenlandia diffusa* Willd, *Rheum undulatum* or *Broussonetia kazinoki* extract alone. Accordingly, the whitening composition for external skin application according to this disclosure may be used in various skin whitening cosmetics.

The disclosed whitening composition for external skin application is used to treat or prevent skin pigment anomaly such as liver spots, freckles, senile spots, etc. Its formulation is not particularly limited. For example, it may be formulated into cosmetics such as nourishing toner, nourishing cream, nourishing lotion, skin lotion, massage cream, pack, foundation, etc. as well as cleansers such as liquid soap, solid soap, facial foam, etc. Individual formulations may include various necessary and adequate ingredients and additives. The kind and amount of the ingredients and additives may be easily determined by those skilled in the art depending on the purpose of use.

MODE FOR INVENTION

The examples and experiments will now be described. The following examples and experiments are for illustrative purposes only and not intended to limit the scope of this disclosure. Those skilled in the art may make changes or modifications thereto.

Preparation Example 1

Preparation of *Oldenlandia diffusa* Willd Extract

Dried whole plant of *Oldenlandia diffusa* Willd (1 kg) is added to purified water (10 L) and heated to boiling. After heating for 10 more minutes and removing water, the residual is washed by adding purified water (10 L). After drying with air and adding 70% ethanol (20 L), the residual is warmed and extracted for 24 hours under reflux. After removing solid using an 80-mesh sieve, the residual filtrate is filtered again. Then, solvent is removed from the filtrate by concentrating under reduced pressure. About 50 g of green solid is obtained.

Preparation Example 2

Preparation of *Broussonetia kazinoki* Extract

Stem and root of *Broussonetia kazinoki* (1 kg) are washed with clean water, dried, and added to water (10 L). After extracting for 5 hours in an extractor equipped with a cooling condenser, the extract is filtered through 300-mesh filter cloth, aged for 5 days at 5-15, and filtered through filter paper. The extract is concentrated under reduced pressure using a distiller equipped with a cooling condenser. About 70 g of solid is obtained.

Preparation Example 3

Preparation of *Rheum undulatum* Extract

95% or higher purity methanol (4 L) is added to dried *Rheum undulatum* (1 kg), which is allowed to stand at room temperature for a day for extraction. This procedure is repeated 2 times. The obtained extract is filtered and concentrated using a vacuum concentrator. 400 g of dry solid is obtained. Water (1 L) and ethyl acetate (2 L) are added to the dry solid (400 g). After stirring at room temperature for 2 hours, the solution is allowed to stand for phase separation. In order to obtain crystal produced at the interface or in the ethyl acetate layer, the aqueous layer is removed and ethyl acetate (2 L) is further added. After repeating this procedure 2 times, followed by sufficient washing and filtration, the filtrate is dried in a vacuum oven. About 30 g of *Rheum undulatum* extract is obtained.

Example 1

The extracts prepared in Preparation Examples 1 to 3 are mixed at a weight ratio of *Oldenlandia diffusa* Willd:*Rheum undulatum*:*Broussonetia kazinoki*=1:1:1.

Example 2

The extracts prepared in Preparation Examples 1 and 2 are mixed at a weight ratio of *Oldenlandia diffusa* Willd:*Broussonetia kazinoki*=1:1.

Example 3

The extracts prepared in Preparation Examples 1 and 3 are mixed at a weight ratio of *Oldenlandia diffusa* Willd:*Rheum undulatum*=1:1.

Comparative Examples 1-3

Each of the extracts prepared in Preparation Examples 1 to 3 is used alone, respectively.

Test Example 1

Melanogenesis Inhibition Effect

1) Test method

Tyrosinase extracted from mushroom (Sigma) is used. Tyrosine is dissolved in distilled water to make 0.3 mg/mL solution. After adding the solution to a test tube, 1.0 mL per each, potassium phosphate buffer (0.1 M, pH 6.8, 1.0 mL) and distilled water (0.7 mL) are added to prepare a mixture solution. An extract sample solution (0.2 mL) prepared by adding each extract of Examples and Comparative Examples to ethanol is added to the mixture solution and reacted in a constant-temperature bath of 37 for 10 minutes. For a control group, only ethanol (0.2 mL) is added, without the extract of Examples or Comparative Examples. After adding 2,500 unit/mL tyrosinase solution (0.1 mL), reaction is further carried out in a constant-temperature bath of 37 for 10 minutes. Then, the test tube containing the reaction solution is rapidly cooled in icy water to stop the reaction, and absorbance is measured at 475 nm using a photoelectric spectrophotometer. Tyrosinase inhibition effect, i.e. the melanogenesis inhibition effect, of the extracts of Examples or Comparative Examples is calculated according to Equation 1. The result is given in Table 1.

$$\text{Melanogenesis inhibition (\%)} = [(A-B)/A] \times 100 \quad \text{Equation 1}$$

A: Light absorbance by cells cultured in medium containing test substance (inhibitor)

B: Light absorbance by cells cultured in medium not containing test substance (inhibitor)

TABLE 1

| | Melanogenesis inhibition (%) | |
|---|---|---|
| | Test substance | Melanogenesis inhibition (%) |
| 1 | Non-treated (control) | 0 |
| 2 | *Oldenlandia diffusa* Willd extract (Comparative Example 1) | 43.2 ± 6.76 |
| 3 | *Broussonetia kazinoki* extract (Comparative Example 2) | 45.4 ± 4.29 |
| 4 | *Rheum undulatum* extract (Comparative Example 3) | 41.8 ± 5.92 |
| 5 | *Oldenlandia diffusa* Willd + *Rheum undulatum* + *Broussonetia kazinoki* (Example 1) | 82.7 ± 6.81 |
| 6 | *Oldenlandia diffusa* Willd + *Broussonetia kazinoki* (Example 2) | 63.2 ± 3.60 |
| 7 | *Oldenlandia diffusa* Willd + *Rheum undulatum* (Example 3) | 72.9 ± 7.82 |

As seen in Table 1, melanogenesis inhibition effect increases by about 2 times when *Oldenlandia diffusa* Willd extract and *Rheum undulatum* extract, *Oldenlandia diffusa* Willd extract and *Broussonetia kazinoki* extract, or *Oldenlandia diffusa* Willd extract, *Rheum undulatum* extract and *Broussonetia kazinoki* extract are used together, as compared to when they are used alone.

Test Example 2

Skin Whitening Effect

On the upper arm of 12 healthy men, opaque tape having a 1.5 cm×1.5 cm hole is attached. Ultraviolet ray (UVB) is irradiated thereon at a dose of about 1.5 to 2 times the minimal erythemal dose of each subject to induce skin blackening.

After UV irradiation, each extract of Comparative Examples 1 to 3 and Examples 1 to 3 prepared into a nourishing cream is applied as a test substance. At one site, nothing is applied (control). Then, change in skin color is observed for 8 weeks. At weeks 4, 6 and 8, skin color is measured using a colorimeter CR2002 (Minolta, Japan). Then, the difference of skin color (L*) between the point when the application is started and is completed is calculated according to Equation 2. The result is shown in Table 2. Skin whitening effect is determined by comparison of L* between the sample applied part and the control.

$$L^* = L^* \text{ at the point when the application is completed} - L^* \text{ at the point when the application is started} \quad \text{Equation 2}$$

TABLE 2

| | Skin whitening effect (L*) | |
|---|---|---|
| | Test substance | ΔL* |
| 1 | Control | 0.46 ± 0.13 |
| 2 | *Oldenlandia diffusa* Willd extract (Comparative Example 1) | 1.23 ± 0.37 |
| 3 | *Broussonetia kazinoki* extract (Comparative Example 2) | 1.12 ± 0.29 |
| 4 | *Rheum undulatum* extract (Comparative Example 3) | 1.09 ± 0.17 |
| 5 | *Oldenlandia diffusa* Willd + *Rheum undulatum* + *Broussonetia kazinoki* (Example 1) | 2.07 ± 0.81 |

TABLE 2-continued

| Skin whitening effect (L*) | | |
|---|---|---|
| | Test substance | ΔL* |
| 6 | *Oldenlandia diffusa* Willd + *Broussonetia kazinoki* (Example 2) | 1.47 ± 0.60 |
| 7 | *Oldenlandia diffusa* Willd + *Rheum undulatum* (Example 3) | 1.58 ± 0.82 |

As seen in Table 2, skin whitening effect increases by about 2 times when *Oldenlandia diffusa* Willd extract and *Rheum undulatum* extract, *Oldenlandia diffusa* Willd extract and *Broussonetia kazinoki* extract, or *Oldenlandia diffusa* Willd extract, *Rheum undulatum* extract and *Broussonetia kazinoki* extract are used together, as compared to when they are used alone.

As demonstrated above, the compositions comprising *Oldenlandia diffusa* Willd extract and *Rheum undulatum* extract, *Oldenlandia diffusa* Willd extract and *Broussonetia kazinoki* extract, or *Oldenlandia diffusa* Willd extract, *Rheum undulatum* extract have 1.5 to 2 times superior melanogenesis inhibition and skin whitening effect, as compared to those comprising *Oldenlandia diffusa* Willd extract or *Rheum undulatum* extract alone. Therefore, they may be used in skin whitening cosmetics.

Formulation Example 1

Nourishing Toner

A nourishing toner is prepared by mixing the ingredients described in Table 3 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 3

| Ingredients | Content (wt %) |
|---|---|
| Purified water | residual |
| Glycerine | 8.0 |
| Butylene glycol | 4.0 |
| Hyaluronic acid extract | 5.0 |
| β-glucan | 7.0 |
| Carbomer | 0.1 |
| *Oldenlandia diffusa* Willd, *Rheum undulatum* and *Broussonetia kazinoki* extract | 0.05 |
| Caprylic/capric triglyceride | 8.0 |
| Squalene | 5.0 |
| Cetearyl glucoside | 1.5 |
| Sorbitan stearate | 0.4 |
| Cetearyl alcohol | 1.0 |
| Antiseptic | adequate |
| Fragrance | adequate |
| Pigment | adequate |
| Triethanolamine | 0.1 |

Formulation Example 2

Nourishing Lotion

A nourishing lotion is prepared by mixing the ingredients described in Table 4 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 4

| Ingredients | Content (wt %) |
|---|---|
| Purified water | residual |
| Glycerine | 3.0 |
| Butylene glycol | 3.0 |
| Liquid Paraffin | 5.0 |
| β-glucan | 7.0 |
| Carbomer | 0.1 |
| *Oldenlandia diffusa* Willd, *Rheum undulatum* and *Broussonetia kazinoki* extract | 3.0 |
| Caprylic/capric triglyceride | 3.0 |
| Squalene | 5.0 |
| Cetearyl glucoside | 1.5 |
| Sorbitan stearate | 0.4 |
| Polysorbate 60 | 1.5 |
| Antiseptic | adequate |
| Fragrance | adequate |
| Pigment | adequate |
| Triethanolamine | 0.1 |

Formulation Example 3

Nourishing Cream

A nourishing cream is prepared by mixing the ingredients described in Table 5 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 5

| Ingredients | Content (wt %) |
|---|---|
| Purified water | residual |
| Glycerine | 3.0 |
| Butylene glycol | 3.0 |
| Liquid paraffin | 7.0 |
| β-glucan | 7.0 |
| Carbomer | 0.1 |
| *Oldenlandia diffusa* Willd, *Rheum undulatum* and *Broussonetia kazinoki* extract | 3.0 |
| Caprylic/capric triglyceride | 3.0 |
| Squalene | 5.0 |
| Cetearyl glucoside | 1.5 |
| Sorbitan stearate | 0.4 |
| Polysorbate 60 | 1.2 |
| Antiseptic | adequate |
| Fragrance | adequate |
| Pigment | adequate |
| Triethanolamine | 0.1 |

Formulation Example 4

Massage Cream

A massage cream is prepared by mixing the ingredients described in Table 6 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 6

| Ingredients | Content (wt %) |
|---|---|
| Purified water | residual |
| Glycerine | 8.0 |

TABLE 6-continued

| Ingredients | Content (wt %) |
|---|---|
| Butylene glycol | 4.0 |
| Liquid paraffin | 45.0 |
| β-glucan | 7.0 |
| Carbomer | 0.1 |
| *Oldenlandia diffusa* Willd, *Rheum undulatum* and *Broussonetia kazinoki* extract | 1.0 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Antiseptic | adequate |
| Fragrance | adequate |
| Pigment | adequate |
| Paraffin | 1.5 |

Formulation Example 5

Pack

A pack is prepared by mixing the ingredients described in Table 7 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 7

| Ingredients | Content (wt %) |
|---|---|
| Purified water | residual |
| Glycerine | 4.0 |
| Polyvinyl alcohol | 15.0 |
| Hyaluronic acid extract | 5.0 |
| β-glucan | 7.0 |
| Allantoin | 0.1 |
| *Oldenlandia diffusa* Willd, *Rheum undulatum* and *Broussonetia kazinoki* extract | 0.5 |
| Nonyl phenyl ether | 0.4 |
| Polysorbate 60 | 1.2 |
| Antiseptic | adequate |
| Fragrance | adequate |
| Pigment | adequate |
| Ethanol | 6.0 |

Formulation Example 6

Ointment for External Skin Application

An ointment is prepared by mixing the ingredients described in Table 8 according to a commonly used method. *Oldenlandia diffusa* Willd and *Rheum undulatum* extract, or *Oldenlandia diffusa* Willd and *Broussonetia kazinoki* extract may be used instead of *Oldenlandia diffusa* Willd, *Rheum undulatum* and *Broussonetia kazinoki* extract.

TABLE 8

| Ingredients | Content (wt %) |
|---|---|
| Purified water | residual |
| Glycerine | 8.0 |
| Butylene glycol | 4.0 |
| Liquid paraffin | 15.0 |
| β-glucan | 7.0 |
| Carbomer | 0.1 |
| *Oldenlandia diffusa* Willd, *Rheum undulatum* and *Broussonetia kazinoki* extract | 1.0 |
| Caprylic/capric triglyceride | 3.0 |
| Squalene | 1.0 |
| Cetearyl glucoside | 1.5 |
| Sorbitan stearate | 0.4 |
| Cetearyl alcohol | 1.0 |
| Antiseptic | adequate |
| Fragrance | adequate |
| Pigment | adequate |
| Beeswax | 4.0 |

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for whitening skin comprising administering to the skin of a subject in need thereof an effective amount of a combination of *Oldenlandia diffusa* Willd extract, *Rheum undulatum* extract and *Broussonetia kazinoki* extract.

2. The method for whitening skin according to claim 1, wherein, the *Oldenlandia diffusa* Willd extract and the *Rheum undulatum* extract are comprised at a weight ratio of 1:0.25-4.

3. The method for whitening skin according to claim 1, wherein the *Oldenlandia diffusa* Willd extract and the *Broussonetia kazinoki* extract are comprised at a weight ratio of 1:0.25-4.

4. The method for whitening skin according to claim 1, wherein, the *Oldenlandia diffusa* Willd extract, the *Rheum undulatum* extract and the *Broussonetia kazinoki* extract are comprised at a weight ratio of 1:0.25-4:0.25-4.

* * * * *